(12) United States Patent
Takayanagi (10) Patent No.: US 10,286,592 B2
(45) Date of Patent: May 14, 2019

(54) PARISON FOREIGN MATTER DETECTION SYSTEM (71) Applicant: YACHIYO INDUSTRY CO., LTD., Saitama (JP)

(72) Inventor: Masateru Takayanagi, Saitama (JP)

(73) Assignee: YACHIYO INDUSTRY CO., LTD., Saitama (JP)

( * ) Notice: Subject to any disclaimer, the term of this patent is extended or adjusted under 35 U.S.C. 154(b) by 0 days.

(21) Appl. No.: 15/760,592

(22) PCT Filed: Jul. 29, 2016

(86) PCT No.: PCT/JP2016/072284
§ 371 (c)(1),
(2) Date: Mar. 15, 2018

(87) PCT Pub. No.: WO2017/047250
PCT Pub. Date: Mar. 23, 2017

(65) Prior Publication Data
US 2018/0250870 A1    Sep. 6, 2018

(30) Foreign Application Priority Data

Sep. 15, 2015  (JP) ................................ 2015-181878

(51) Int. Cl.
*B29C 49/78*    (2006.01)
*B29B 11/00*    (2006.01)
(Continued)

(52) U.S. Cl.
CPC .............. *B29C 49/78* (2013.01); *B29B 11/00* (2013.01); *B29C 31/08* (2013.01); *B29C 48/92* (2019.02);
(Continued)

(58) Field of Classification Search
CPC ............ B29C 49/78; B29C 2949/7821; B29C 2949/78386; B29C 2949/78722
See application file for complete search history.

(56) References Cited

U.S. PATENT DOCUMENTS

2006/0163778 A1* 7/2006 Maziers ............... B29C 47/0023
264/409
2012/0007289 A1* 1/2012 O'Connell ............. B29C 49/04
264/406

FOREIGN PATENT DOCUMENTS

DE    102008052608 B3 *  5/2010   ............. B29C 49/70
JP    59-31437 A    2/1984
(Continued)

OTHER PUBLICATIONS

Partial machine translation of JP 2014-134461 A dated Jul. 2014 obtained from the espace website. (Year: 2014).*
(Continued)

*Primary Examiner* — Robert B Davis
(74) *Attorney, Agent, or Firm* — Kenealy Vaidya LLP (57) ABSTRACT

Some embodiments are directed to a system for detecting foreign matter in a parison discharged successively from a discharge device, the system comprising: infrared cameras that detect infrared beams emitted from the parison; and a determination unit that determines whether foreign matter is present in the parison on the basis of the infrared beams detected by the infrared cameras. A determination area is set in the parison in a discharge direction of the parison, a storage unit is provided that stores an infrared threshold set for the determination area, and the determination unit compares the detected values from the infrared cameras with the threshold.

5 Claims, 6 Drawing Sheets

(51) Int. Cl.
    *B29C 31/08*     (2006.01)
    *G01N 21/84*     (2006.01)
    *B29C 49/80*     (2006.01)
    *B29C 51/46*     (2006.01)
    *B29C 48/92*     (2019.01)
    *B29C 49/04*     (2006.01)
    *G01N 21/90*     (2006.01)
    *B29C 49/42*     (2006.01)
    *B29C 51/02*     (2006.01)
    *B29C 48/09*     (2019.01)
    *B29C 48/00*     (2019.01)

(52) U.S. Cl.
    CPC .............. *B29C 49/80* (2013.01); *B29C 51/46* (2013.01); *G01N 21/84* (2013.01); *B29C 48/0017* (2019.02); *B29C 48/0022* (2019.02); *B29C 48/09* (2019.02); *B29C 49/04* (2013.01); *B29C 49/4205* (2013.01); *B29C 51/02* (2013.01); *B29C 2793/0027* (2013.01); *B29C 2793/0063* (2013.01); *B29C 2948/92295* (2019.02); *B29C 2948/92304* (2019.02); *B29C 2948/92428* (2019.02); *G01N 21/909* (2013.01); *G01N 21/9081* (2013.01)

(56) References Cited

FOREIGN PATENT DOCUMENTS

| | | |
|---|---|---|
| JP | H03-82504 A | 4/1991 |
| JP | H09-234783 A | 9/1997 |
| JP | 2000-146851 | 5/2000 |
| JP | 2014-134461 A | 7/2014 |

OTHER PUBLICATIONS

International Search Report and Written Opinion of the International Search Report for PCT/JP2016/072284 dated Sep. 27, 2016.
Preliminary Report on Patentability of the International Search Report for PCT/JP2016/072284 dated Aug. 8, 2017.

\* cited by examiner

DISCHARGE DIRECTION

PARISON FOREIGN MATTER DETECTION SYSTEM

CROSS-REFERENCE TO RELATED APPLICATIONS

This application is a U.S. National Stage Application under 35 U.S.C. § 371 of International Patent Application No. PCT/JP2016/072284 file Jul. 29, 2016, which claims the benefit of priority to Japanese Patent Application No. 2015-181878 filed 15 Sep. 2015, the disclosures of all of which are hereby incorporated by reference in their entireties.

TECHNICAL FIELD

The present invention relates to a parison foreign matter detection system.

BACKGROUND ART

Patent Literature 1 discloses a conventional technique for detecting foreign matter in a parison. Patent Literature 1 states that: a CCD camera captures an image of the parison; and whether the foreign matter is present in the parison is detected by electrically processing the image data of the parison.

CITATION LIST

Patent Literature

Patent Literature 1: Japanese Patent Application Publication No. S59-31437

SUMMARY OF INVENTION

Technical Problem

The technique disclosed in Patent Literature 1, however, requires the parison to be transparent. This technique, therefore, involves a problem that when the parison is opaque, no foreign matter can be detected from the parison.

The present invention has been made to solve such a problem. An object of the present invention is to provide a parison foreign matter detection system that is capable of detecting whether foreign matter exists in a parison even when the parison is opaque.

Solution to Problem

To solve the above problems, the present invention is a system for detecting foreign matter in a parison that is successively discharged from a discharge device. The present invention is characterized in that the system includes: an infrared camera for detecting infrared rays emitted from the parison; and a determination unit for determining whether foreign matter exists in the parison based on the infrared rays detected by the infrared camera.

According to the present invention, since the infrared rays emitted from the prison are detected, the foreign matter in the parison can be detected even when the parison is opaque.

In addition, the present invention is characterized in that: a determination area is set partially in the parison; the system further includes a storage unit for storing an infrared threshold set for the determination area; and the determination unit compares a detection value from the infrared camera with the threshold.

According to the present invention, since a range in which to detect the foreign matter can be limited to a desired range, unnecessary occurrence of a defective molded product can be inhibited.

Furthermore, the present invention is characterized in that multiple determination areas with different thresholds are set.

According to the present invention, since a degree of tolerance to the foreign matter is made different between the determination areas, the unnecessary occurrence of a defective molded product can be inhibited to a greater degree.

Moreover, the present invention is characterized in that: a non-determination area, where no determination is made, is further set partially in the parison; and the determination area is that which includes a part on which to mount a component.

According to the present invention, the unnecessary occurrence of a defective molded product can be inhibited while the part on which to mount the component is prevented from being affected by the foreign matter.

Besides, the present invention is characterized in that the system further includes a control unit for issuing an instruction to discard the parison when the determination unit determines that the foreign matter exists in the parison.

Since the system includes the control unit for issuing the instruction to discard the parison when the determination unit determines that the foreign matter exists in the parison, the system is capable of discarding the defective parison using the simple configuration.

In addition, the present invention is characterized in that the control unit issues the discard instruction to a conveyer for conveying the parison as cut away.

According to the present invention, the use of the conveyer makes it possible to discard the defective parison using the simpler configuration.

Furthermore, the present invention is characterized in that: the parison discharged from the discharge device has a shape of an arc in a plan cross-sectional view; and multiple infrared cameras are arranged surrounding the parison.

According to the present invention, all the circumference of the parison having the shape of an arc in the plan cross-sectional view can be designated as target areas of the infrared detection.

Advantageous Effects of Invention

According to the present invention, since infrared rays emitted from a prison are detected, foreign matter in the parison can be detected even when the parison is opaque.

DESCRIPTION OF EMBODIMENTS

Figure 1:
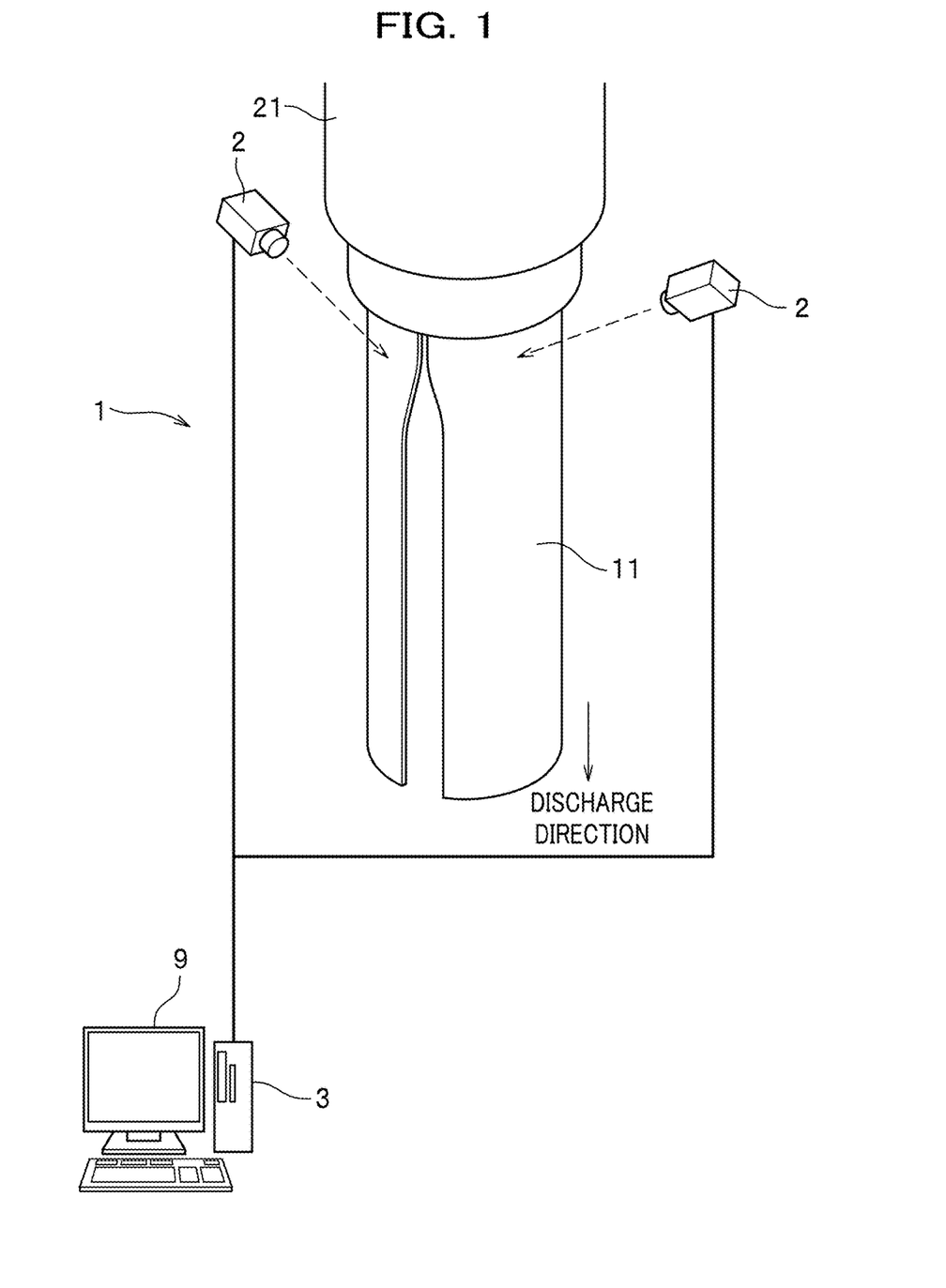
FIG. 1 is an external view of a parison foreign matter detection system according to the present invention.
Figure 2:
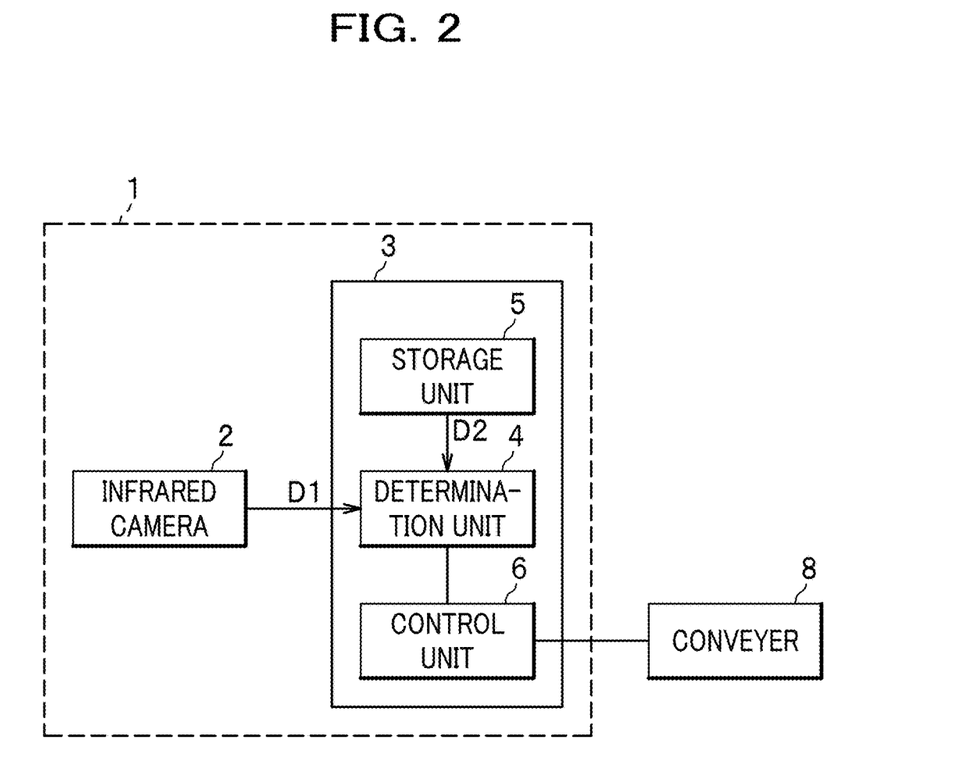
FIG. 2 is a block diagram of a configuration of the parison foreign matter detection system according to the present invention.

In FIG. 1, a parison foreign matter detection system 1 according to the present invention is a system for detecting foreign matter 12 (FIG. 3) in a parison 11 that is successively discharged from a discharge device 21. The parison foreign matter detection system 1 includes: infrared cameras 2 for detecting infrared rays emitted from the parison 11; and a controller 3. As illustrated in FIG. 2, the controller 3 includes a determination unit 4, a storage unit 5 and a control unit 6. A personal computer may be used as the controller 3.

The discharge device 21 includes a die and a core. The parison 11 is discharged downward from an annular discharge port that is formed in a bottom surface of the discharge device 21, and is formed in the shape of a cylinder. FIG. 1 shows that the parison 11 extends downward after cut, by a cutter (not illustrated) disposed in the discharge port of the discharge device 21, into halves, that is to say, a pair of parison pieces each formed in the shape of a semicircular arc in a plan cross-sectional view. A pair of infrared cameras 2 are provided at positions around the parison 11 that are substantially diametrically opposite to each other, in order that the infrared cameras 2 can capture images of the parison pieces respectively. The shape of the parison of the present invention, however, is not limited to this. The parison 11 may be discharged downward as remaining in the cylindrical shape without cut into halves. Otherwise, the parison 11 may be discharged downward in a substantially flat shape.

Figure 3:
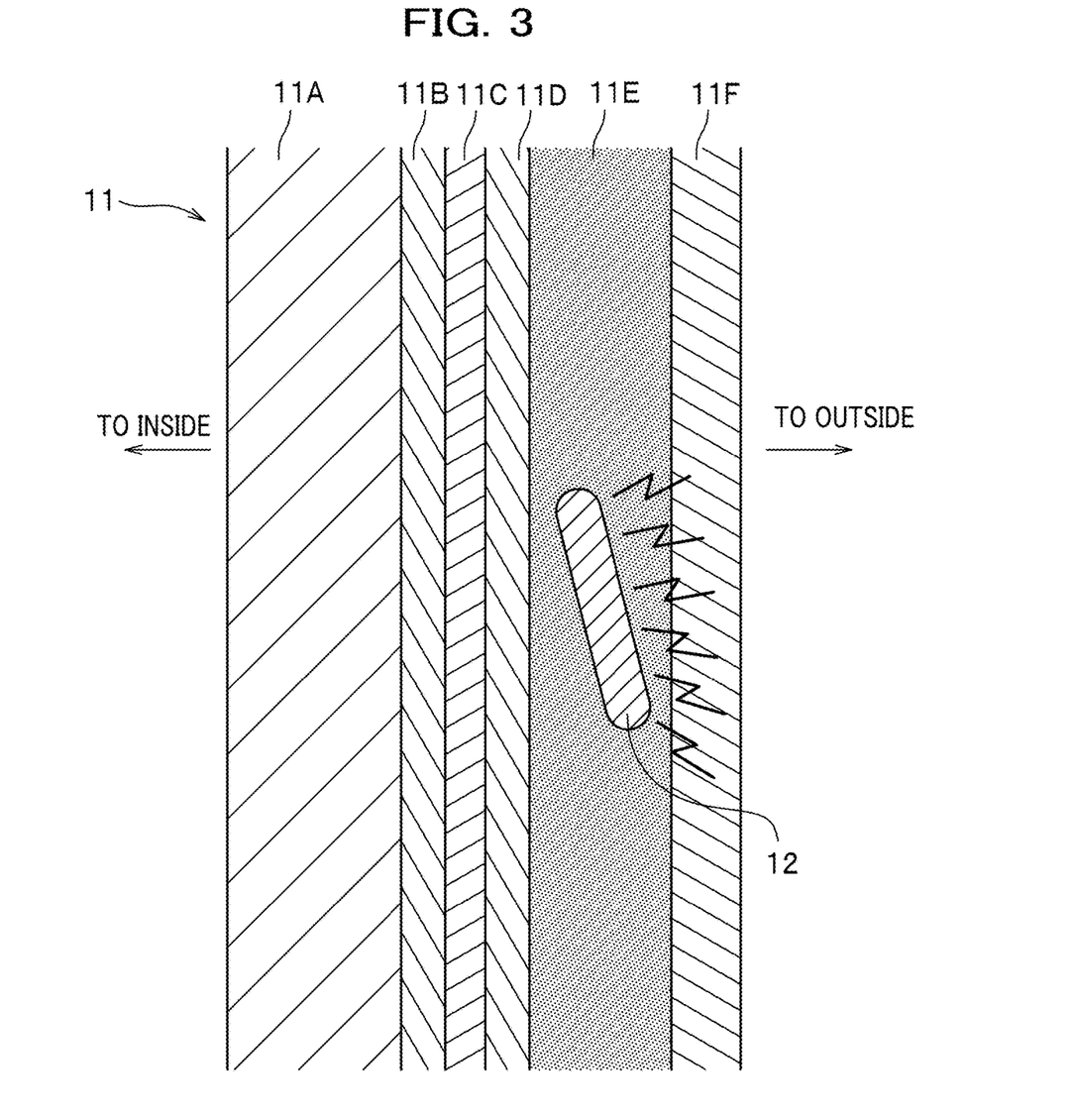
FIG. 3 is a cross-sectional view of a layer configuration of a parison.

FIG. 3 illustrates an example of a layer configuration of the parison 11 in a case where a product made from the parison 11 is a vehicular fuel tank. In order from the inside of the tank, the layer configuration includes six layers of four types: a thermoplastic resin layer 11A, a bonding layer 11B, a barrier layer 11C, a bonding layer 11D, a recycling layer 11E, and a thermoplastic resin layer 11F. The thermoplastic resin layers 11A, 11F are made, for example, of HDPE (high-density polyethylene). The barrier layer 11C is made of a material good at fuel impermeability, for example, EVOH (ethylene-vinyl alcohol copolymer). The recycling layer 11E is made from a recycled material that is obtained by melting and blending burrs coming from deburring fuel tanks, and fuel tanks rejected in the molding process or the inspection process.

The foreign matter 12 exists mainly in the recycling layer 11E. Since the parison 11 is opaque, the foreign matter 12 in the recycling layer 11E is difficult to identify in visual inspection. The infrared cameras 2 are capable of effectively detecting the foreign matter 12, even in a case where the parison 11 is opaque, since the infrared cameras 2 detect infrared rays emitted from the foreign matter 12. An amount of infrared energy emitted from an object is expressed by the following equation (1)

$$Q = \varepsilon \cdot \sigma \cdot T^4 \quad \text{Equation (1)}$$

where: Q is an amount of infrared energy [W/m$^2$]; $\varepsilon$ is an emissivity; $\sigma$ is the Stefan-Boltzmann constant, $5.67 \times 10^{-8}$ [W/m$^2$K$^4$]; and T is absolute temperature [K].

Figure 4:
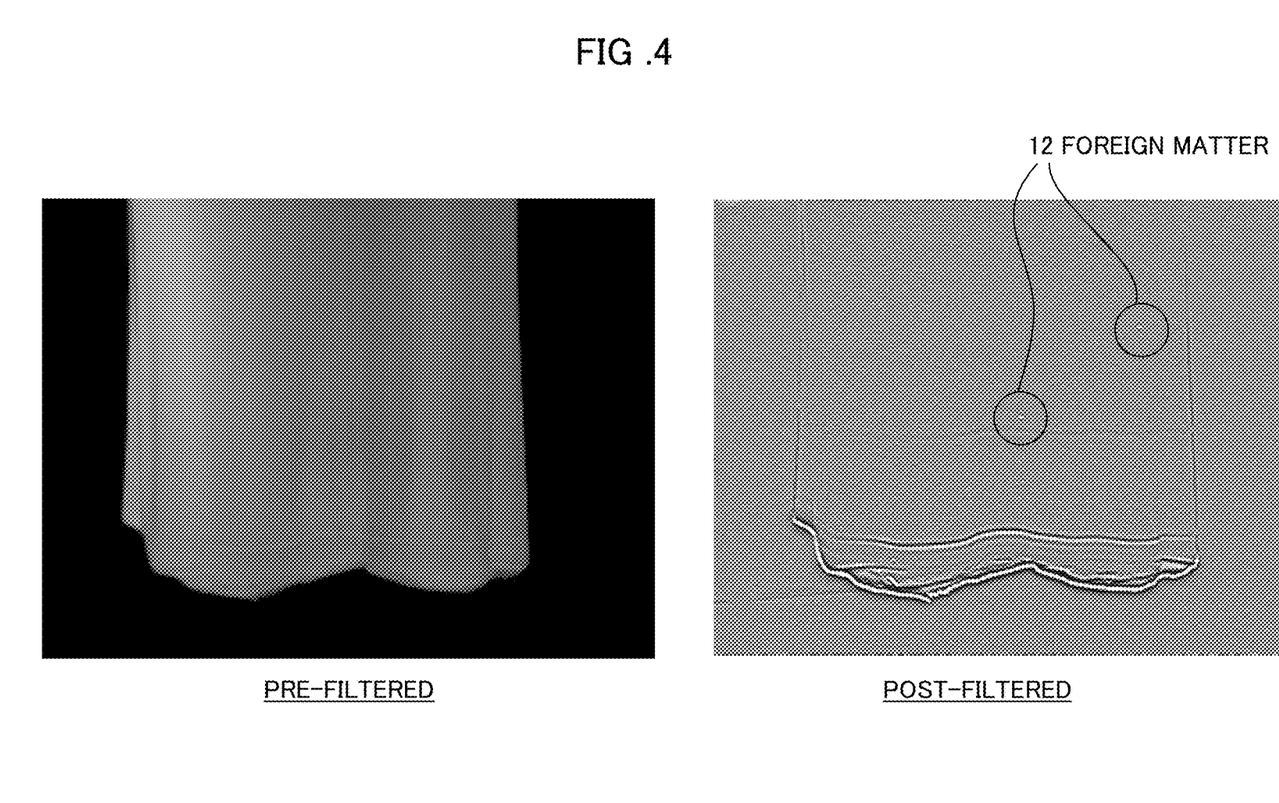
FIG. 4 shows images of temperature distributions taken by an infrared camera.

Examples of the foreign matter 12 contained in the recycling layer 11E includes: contaminants from the outside; and substances stemming from oxidative deterioration of EVOH of the barrier layer 11C, as well as polyethylene of the thermoplastic resin layers 11A, 11F. The emissivity $\varepsilon$ in Equation (1) is a value that varies depending on the material and surface condition of the object. Accordingly, when the emissivity $\varepsilon$ of the foreign matter 12 is different from that of the recycling layer 11E, only the amount of infrared energy emitted from a place where the foreign matter 12 exists is changed. Thus, it is possible to identify the foreign matter 12 by detecting the amount of infrared energy emitted from the foreign matter 12 using the infrared cameras 2. To put it specifically, each infrared camera 2 includes: a detection element for absorbing infrared rays (7.5 µm to 13 µm) from electromagnetic waves; and a temperature sensor for detecting a change in the temperature of the detection element that raises its temperature by absorbing the infrared rays. Based on distribution of temperature detected by the temperature sensor, the infrared camera 2 outputs to the outside a signal representing an image of the distribution of temperature in an image capturing area. FIG. 4 shows temperature distribution images that are obtained by capturing an image of a lower part of the cylindrical parison and its vicinity using one infrared camera 2, and that are displayed on a monitor 9 (FIG. 1). FIG. 4A shows a pre-filtered image, and FIG. 4B shows a post-filtered image. The filtering makes it possible to visually check on the monitor 9 whether the foreign matter 12 exists therein.

Figure 5:
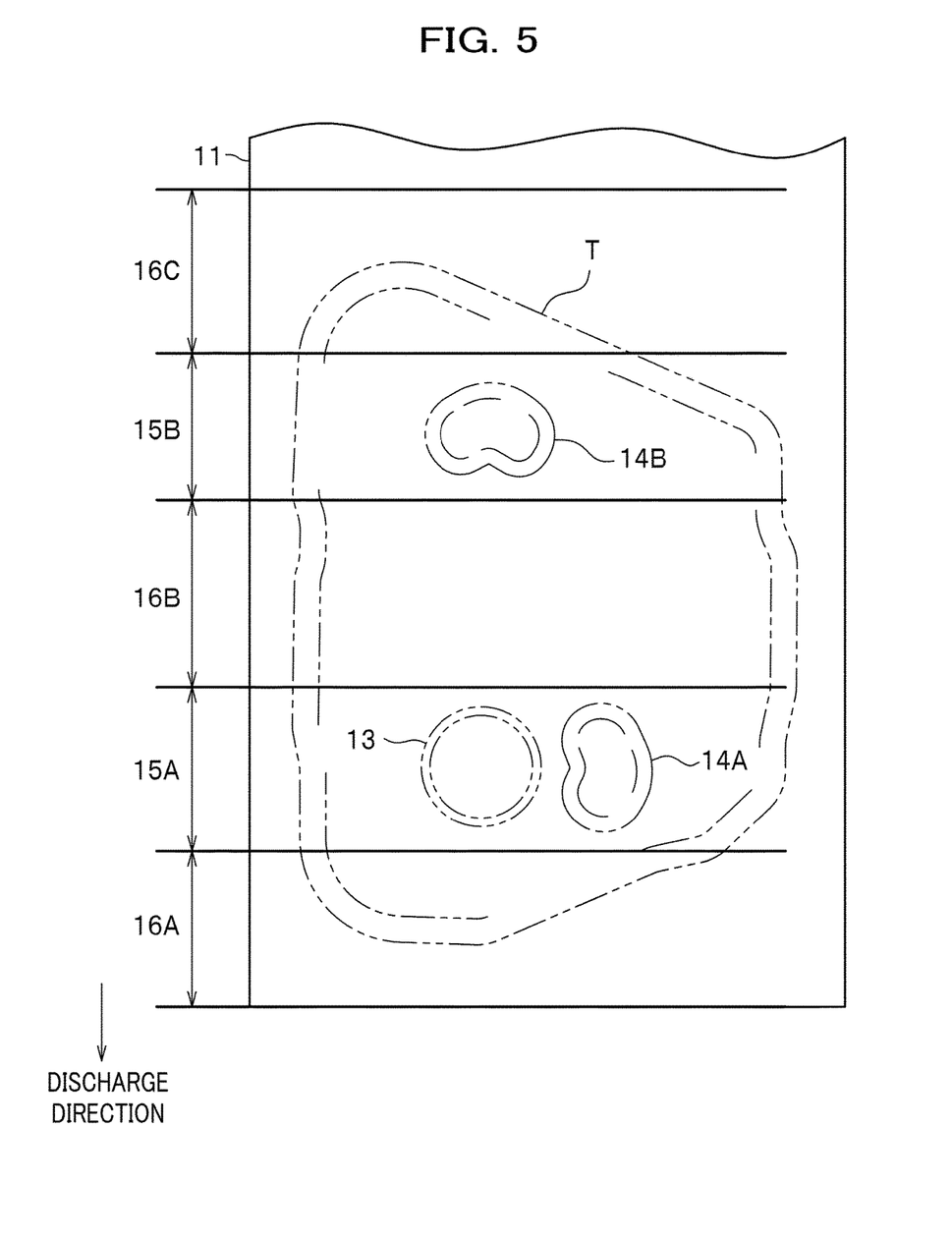
FIG. 5 is a plan view illustrating determination areas and non-determination areas that are set in a fuel tank.

In FIG. 2, the determination unit 4 determines whether the foreign matter 12 exists in the parison 11, based on detection values D1 from the infrared cameras 2, specifically signals representing the above-discussed temperature distribution images. In FIG. 5, the fuel tank T, a product made from the parison, includes: a pump mounting seat 13 formed thereon, on which a fuel pump (not illustrated) is mounted; and absorber mounting seats 14A, 14B formed thereon, on which the two respective ends of an absorber (not illustrated) for inhibiting foaming of fuel inside the tank are mounted. In a case where the foreign matter 12 exists in a pump mounting seat 13-forming area and absorber mounting seats 14A, 14B-forming areas, there is likelihood that the pump mounting seat 13 and the absorber mounting seats 14A, 14B have a defective shape, and accordingly hinder the fuel pump and the absorber from being mounted thereon. On the other hand, the existence of the foreign matter 12 in the other areas on which no components are mounted does not cause a serious problem in some cases.

In this case, it is desirable that determination areas are set partially in the parison, respectively. In the embodiment, determination areas and non-determination areas are set in the parison 11 with a predetermine length (a length enough to form a single molded product such as a fuel tank) in a way that arranges the areas in a discharge direction of the parison 11. The determination areas are those on which the determination unit 4 makes determination. The non-determination areas are those on which the determination unit 4 makes no determination. FIG. 5 shows an example where in order from the downstream to the upstream in the discharge direction of the parison 11, a non-determination area 16A, a determination area 15A, an non-determination area 16B, a determination area 15B and a non-determination area 16C are set in the parison 11. The determination area 15A is that including the pump mounting seat 13 and the absorber mounting seat 14A. The determination area 15B is that including the absorber mounting seat 14B. In other words, the determination areas 15A, 15B are those including the parts on which to mount the components. The non-determination areas 16A to 16C are those including no part on which to mount a component.

In FIG. 2, the storage unit 5 stores infrared thresholds D2 set for the respective determination areas 15A, 15B. The threshold D2 for the determination area 15A and the threshold D2 for the determination area 15B may be equal to, or different from, each other. The determination unit 4 compares the detection values D1 inputted from the infrared cameras 2 with the thresholds D2 stored in the storage unit 5. When either of the detection values D1 is larger than the corresponding threshold value D2, the determination unit 4 determines that the foreign matter 12 exists in the corresponding one of the determination areas 15A, 15B.

Figure 6:
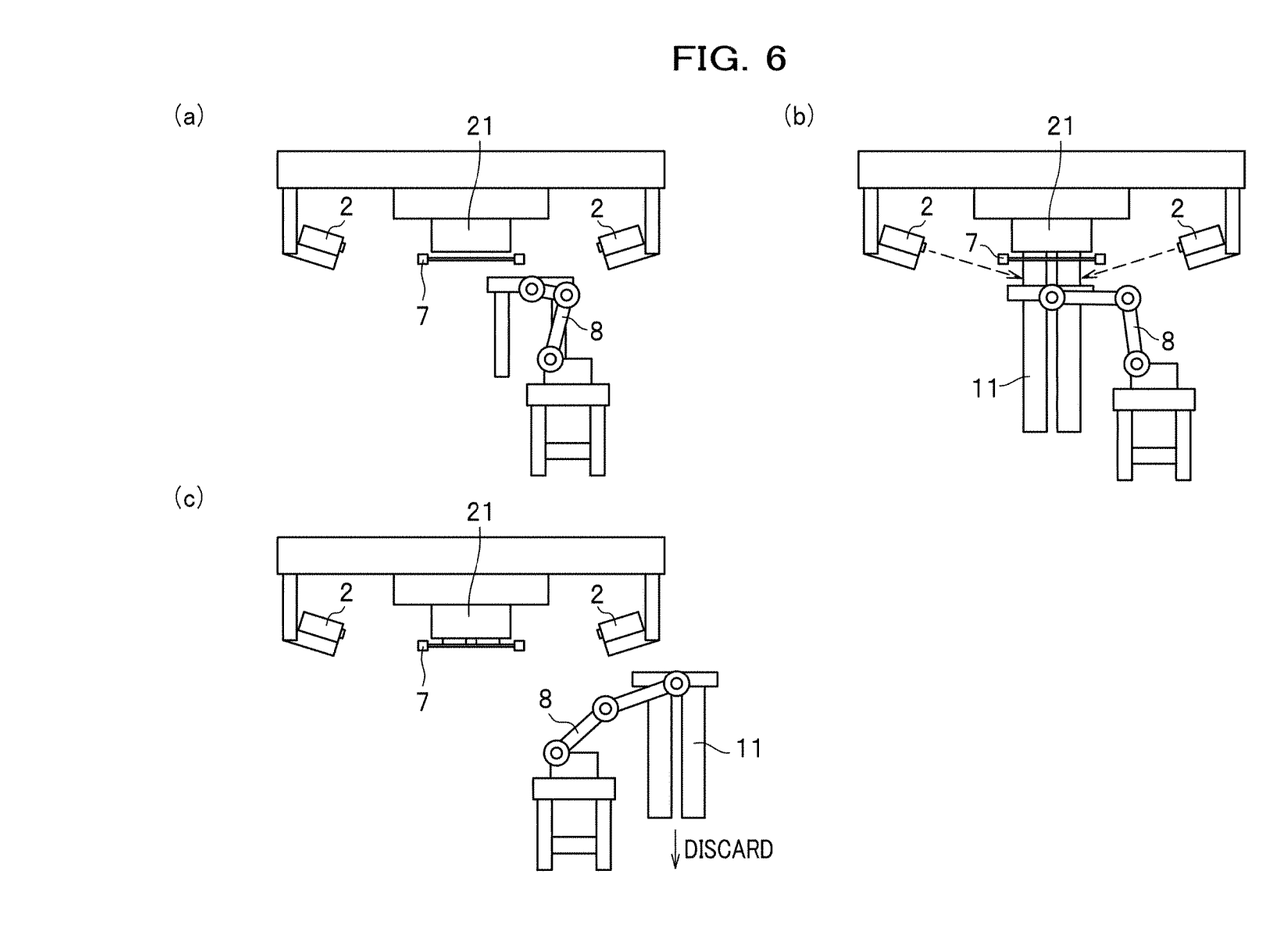
FIGS. 6A to 6C are explanatory diagrams for explaining how the parison foreign matter detection system works.

When the determination unit 4 determines that the foreign matter 12 exists there, the control unit 6 issues an instruction to discard the parison 11 with the predetermined length. A cutter 7 (FIG. 6) for cutting an upper end of the parison 11 after the parison 11 is discharged by the predetermined length, and a conveyer 8 (FIG. 6) for conveying the cut-away parison 11 to a molding apparatus (not illustrated) by gripping the upper end portion of the parison 11 are arranged under the discharge device 21. The control unit 6 issues the discharge instruction to the conveyer 8. Thereby, the conveyer 8 conveys a parison 11 which is defective due to the foreign matter 12 to a predetermined disposal site and discards it there, instead of being sent to the molding apparatus.

[Working]

Descriptions will be provided for how the parison foreign matter detection system 1 works. FIG. 6A shows what condition the parison foreign matter detection system 1 is in before the discharge of the parison 11. The cutter 7 and the conveyer 8 are in their respective standby positions. As illustrated in FIG. 6B, when the parison 11 is discharged, the pair of infrared cameras 2 capture images of upstream external surfaces of the parison 11. The determination unit 4 compares the detection values D1 from the infrared cameras 2 with the thresholds D2 stored in the storage unit 5, and determines whether the foreign matter 12 exits in the determination areas 15A, 15B. Incidentally, the ranges of the determination areas 15A, 15B can be easily identified based on the speed at which the parison 11 is discharged (how long time has passed since the start of the discharge).

In a case where it is determined that no foreign matter 12 exits in either of the determination areas 15A, 15B, the conveyer 8 conveys the cut-away parison 11 with the predetermined length to the molding apparatus. In a case where it is determined that the foreign matter 12 exits in at least one of the determination areas 15A, 15B, the control unit 6 sends the discard instruction to the conveyer 8, and the conveyer 8 conveys the cut-away parison 11 with the predetermined length to the disposal site as illustrated in FIG. 6C.

As discussed above, the system includes the infrared cameras 2 for detecting infrared rays emitted from the parison 11, and the determination unit 4 for determining whether the foreign matter 12 exists in the parison 11 based on the infrared rays detected by the infrared cameras 2. Thus, the system is capable of detecting the foreign matter 12 in the parison 11 even when the parison 11 is opaque.

Furthermore, the system allows the determination areas 15A, 15B to be set partially in the parison 11; the system includes the storage unit 5 for storing the infrared thresholds D2 that are respectively set for the determination areas 15A, 15B; and the determination unit 4 is configured to compare the detection values D1 from the infrared cameras 2 with the thresholds D2. Thus, the system enables the ranges in which to detect the foreign matter 12 to be limited to desired ranges, and is capable of inhibiting unnecessary occurrence of defective molded products. Particularly, the system allows the multiple determination areas 15A, 15B with the mutually different thresholds D2 to be set in the parison 11. Thus, the system makes it possible to make tolerance to the foreign matter different between the determination areas, and accordingly is capable of inhibiting the unnecessary occurrence of defective molded products to a greater degree.

The non-determination areas 16A to 16C, where the system makes no determination, are set partially in the parison 11, and the determination areas 15A, 15B are those including the parts on which to mount the components. Thus, the system is capable of inhibit the unnecessary occurrence of defective molded products while preventing the parts on which to mount the components from being affected by the foreign matter 12.

Since the system includes the control unit 6 for issuing the instruction to discard the parison 11 when the determination unit 4 determines that the foreign matter 12 exists in the parison 11, the system is capable of discarding the defective parison 11 using the simple configuration. Particularly since the control unit 6 is configured to issue the discard instruction to the conveyer 8 which conveys the cut-away parison 11, the system is capable of discarding the defective parison 11 using the simpler configuration.

Since the parison 11 discharged from the discharge device 21 has the shape of an arc (inclusive of the shape of a cylinder) in a plan cross-sectional view and the multiple infrared cameras 2 are arranged surrounding the parison 11, all the circumference of the parison 11 having the shape of an arc in the plan cross-sectional view can be designated as the target areas of the infrared detection.

The foregoing descriptions have been provided for the preferred embodiment of the present invention. Although the discussed embodiment divides the parison 11 with the predetermined length into the determination areas and the non-determination areas, the configuration may be such that: only multiple determination areas, but no non-determination areas, are set in the parison 11; and the thresholds D2 assigned to the respective multiple determination areas are set different from each other.

REFERENCE SIGNS LIST 1 parison foreign matter detection system
2 infrared camera
3 controller
4 determination unit
5 storage unit
6 control unit
7 cutter
8 conveyer
15A, 15B determination area
16A, 16B, 16C non-determination area

The invention claimed is:

1. A system for detecting foreign matter in a parison that is successively discharged from a discharge device, the system comprising:
 a pair of infrared cameras for detecting infrared rays emitted from the parison, and
 a determination unit for determining whether foreign matter exists in the parison based on the infrared rays detected by the infrared cameras,
 a determination area is set partially in the parison,
 the system further comprises a storage unit for storing an infrared threshold set for the determination area,
 the determination unit compares a detection value from the infrared camera with the threshold, and
 the determination area is that which corresponds to a part on which to mount a component to be attached to parison, wherein
the pair of infrared cameras are provided at positions around the parison that are substantially diametrically opposite to each other.

2. The system according to claim 1, wherein a plurality of the determination areas with a plurality of the thresholds different from each other are set.

3. The system according to claim 1, wherein that the system further includes a control unit for issuing an instruction to discard the parison when the determination unit determines that the foreign matter exists in the parison.

4. The system according to claim 3, wherein that the control unit issues the discard instruction to a conveyer for conveying the parison as cut away.

5. The system according to claim 1, wherein:
the parison discharged from the discharge device has a shape of an arc in a plan cross-sectional view, and
a plurality of the infrared cameras are arranged surrounding the parison.

* * * * *